(12) United States Patent
Kim

(10) Patent No.: US 6,656,138 B2
(45) Date of Patent: Dec. 2, 2003

(54) MULTIFUNCTION HYPERTHERMO-THERAPEUTICAL APPARATUS

(75) Inventor: Myeong-su Kim, Incheon (KR)

(73) Assignee: Dwzone Medical Instruments Co., LTD (KR)

( * ) Notice: Subject to any disclaimer, the term of this patent is extended or adjusted under 35 U.S.C. 154(b) by 121 days.

(21) Appl. No.: 10/040,367

(22) Filed: Jan. 9, 2002

(65) Prior Publication Data

US 2003/0130601 A1 Jul. 10, 2003

(51) Int. Cl.[7] .................. A61H 15/02; A61G 10/02; A61M 21/02
(52) U.S. Cl. ................. 601/19; 601/22; 601/99; 601/100; 601/98; 600/21; 600/27
(58) Field of Search .................. 601/16, 49, 17, 601/19, 22, 97, 98, 99, 100, 101, 102, 103, 104, 41, 43; 128/202.12; 4/524; 607/91, 44; 600/21, 27, 28

(56) References Cited

U.S. PATENT DOCUMENTS

| | | | | |
|---|---|---|---|---|
| 4,884,574 A | * | 12/1989 | Hardie et al. | 601/55 |
| 5,024,650 A | * | 6/1991 | Hagiwara et al. | 600/26 |
| 5,101,809 A | * | 4/1992 | Daffer et al. | 601/52 |
| 5,505,691 A | * | 4/1996 | Fenkell | 601/99 |
| 5,645,578 A | * | 7/1997 | Daffer et al. | 607/91 |
| 5,891,186 A | * | 4/1999 | Daffer et al. | 607/91 |
| 6,454,732 B1 | * | 9/2002 | Lee | 601/101 |

FOREIGN PATENT DOCUMENTS

KR 10-2000-0006622 2/2000

* cited by examiner

Primary Examiner—Danton D. DeMille
(74) Attorney, Agent, or Firm—Rothwell Figg Ernst & Manbeck p.c.

(57) ABSTRACT

The present invention relates to a multifunction hyperthermo-therapeutical apparatus, and more particularly, to a multifunction hyperthermo-therapeutical apparatus which basically uses the hyperthermo-therapeutical apparatus and, of course, selectively uses one or more specific appliances according to the selection of a user by installing a sleep aid means, foot pressure means and vertebral correction means with additional functions at the one hyperthermo-therapeutical apparatus, thereby maximizing a hyperthermo-therapeutical curative effect and achieving an optimum sleep, blood circulation and vertebral correction.

8 Claims, 9 Drawing Sheets

MULTIFUNCTION HYPERTHERMO-THERAPEUTICAL APPARATUS

BACKGROUND OF THE INVENTION

1. Field of the Invention

The present invention relates to a multifunction hyperthermo-therapeutical apparatus, and more particularly, to a multifunction hyperthermo-therapeutical apparatus which basically uses the hyperthermo-therapeutical apparatus and, of course, selectively uses one or more specific appliances according to the selection of a user by installing a sleep aid means, foot pressure means and vertebral correction means with additional functions at the one hyperthermo-therapeutical apparatus, thereby maximizing a hyperthermo-therapeutical curative effect and achieving an optimum sleep, blood circulation and vertebral correction.

2. Description of the Related Art

As a general hyperthermo-therapeutical apparatus, there was disclosed a hyperthermo-therapeutical apparatus for applying a hot compress to the affected part (vertebra) of a patient by using a treatment unit (infrared lamp). As shown in FIG. 1, such a hyperthermo-therapeutical apparatus 10 mainly includes a body 20 of a mat type; a reciprocal motor 30 fixed at one side of the interior of the body 20; a driving transmission device (belt, chain and wire) 40 connected to the reciprocal motor 30 and reciprocally moving around a predetermined section when the reciprocal motor 30 is driven; and a treatment unit 50 connected to the driving transmission device 40 in order to move around the predetermined section along with the driving transmission device 40 and applying a hot compress to the vertebral acupuncture point of a patient.

By applying a hot compress to the vertebral acupuncture point of the patient by using such a hyperthermo-therapeutical apparatus 10, the desired end can be achieved. However, since a mat type hyperthermo-therapeutical apparatus commonly used is designed to simply apply a hot compress the vertebral acupuncture point of man without using additional functions, it has limitations in its functions.

Due to this, in order to take a rest or sleep after using the hyperthermo-therapeutical apparatus, a special method has to be employed, which is inconvenient. Moreover, in order to compress foot, a special tool has to be employed, which needs cost.

Furthermore, generally, every motions of man are made in a state that he or she slightly bends forward from the viewpoint of a human body structure. Such motions makes posterior structure and texture of a waist portion, that is, intramuscular ligaments, fascia, posterior longitudinal ligaments, inter-vertebral discs, annular fibers and the like, excessively lengthened to thus reduce the muscle force of the waist, thereby causing a variety of lumbar diseases and resultantly greatly degrading the elasticity of vertebral articulations. Since the prior art hyperthermo-therapeutical apparatus has no device for pulling back the waist of the patient or tightening and relaxing the same, it is impossible to apply a hot compress the vertebral acupuncture point can while simultaneously correcting the vertebral acupuncture point.

SUMMARY OF THE INVENTION

It is, therefore, an object of the present invention to provide a multifunction hyperthermo-therapeutical apparatus in which since the hyperthermo-therapeutical apparatus for applying a hot compress to the vertebral acupuncture point of the user is provided with the sleep aid means, anions and moisture can be supplied into the capsule through the sleep aid means when the sleep aid means is used, thereby maintaining an optimum sleep condition and thus performing a hyperthermo-therapy while having a good sleep.

It is, another object of the present invention to provide a multifunction hyperthermo-therapeutical apparatus in which since the hyperthermo-therapeutical apparatus for applying a hot compress to the vertebral acupuncture point of the user is provided with the foot pressure means, the sole is pressurized when the foot pressure means is used, thereby helping blood circulation.

It is, another object of the present invention to provided a multifunction hyperthermo-therapeutical apparatus in which since the hyperthermo-therapeutical apparatus for applying a hot compress to the vertebral acupuncture point of the user is provided with the vertebral correction means, a hot compress can be applied to the vertebra as in the conventional art and of course the operation of bending the waist of the user backward is repeated to thus tighten and relax the waist, thereby improving the elasticity and muscle force of the vertebral acupuncture point and correcting the vertebra.

To achieve the above object, there is provided a multifunction hyperthermo-therapeutical apparatus comprising: a sleep aid means installed at the portion corresponding to the front surface of the body for generating anions and moisture mostly on the head portion of a user; a foot pressure means installed to the portion corresponding to the rear surface of the body for applying a hot compress on the sole of the user; and a vertebral correction means installed at the center of the body between the sleep aid means and the foot pressure means for raising the waist of the user to a predetermined height and tightening and relaxing the vertebral acupuncture point.

BRIEF DESCRIPTION OF THE DRAWINGS

The above objects, features and advantages of the present invention will become more apparent from the following detailed description when taken in conjunction with the accompanying drawings, in which.

DETAILED DESCRIPTION OF THE PREFERRED EMBODIMENT

Figure 1:
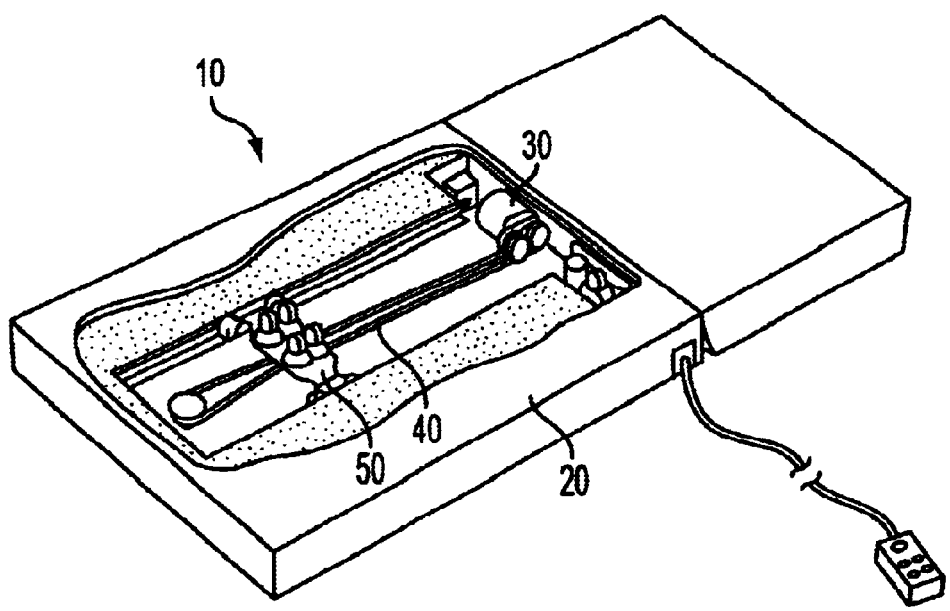
FIG. 1 is a perspective view of the interior of a general hyperthermo-therapeutical apparatus.
Figure 2:
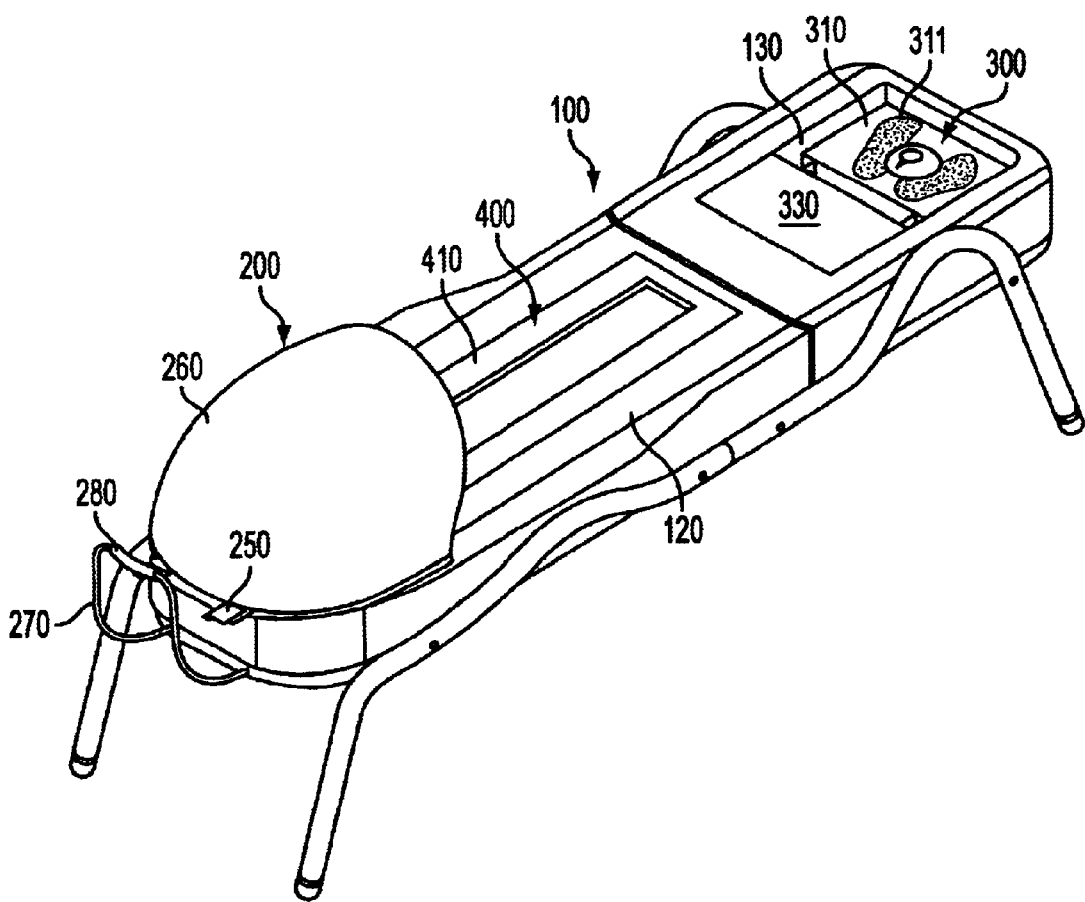
FIG. 2 is a perspective view of the hyperthermo-therapeutical apparatus according to the present invention.

A preferred embodiment of the present invention will now be described with reference to the accompanying drawings.

The construction of a hyperthermo-therapeutical apparatus 100 of the present invention is identical to that of the conventional art in that a treatment unit 110 is installed on a body 120 of a mat type and this treatment unit 110 applies a hot compress to the vertebral acupuncture point of a patient while it is automatically moved around a predetermined section by a driving transmission means.

The present invention is designed to use the hyperthermo-therapeutical apparatus more effectively by adding additional functions to the hyperthermo-therapeutical apparatus 100. As illustrated in FIGS. 1 through 8, in the present invention, firstly, the body 120 is selected and following techniques are used such as a technique for generating anions and moisture mostly on the head portion of a user by installing a sleep aid means 200 at the portion corresponding to the front surface of the body 120, a technique for performing a pressurized fomenation on the sole of the user by installing a foot pressure means 300 to the portion corresponding to the rear surface of the body 120 and a technique for raising the waist of the user to a predetermined height and tightening and relaxing the vertebral acupuncture point by installing a vertebral correction means 400 at the center of the body 120 between the sleep aid means 200 and the foot pressure means 300.

Figure 3:
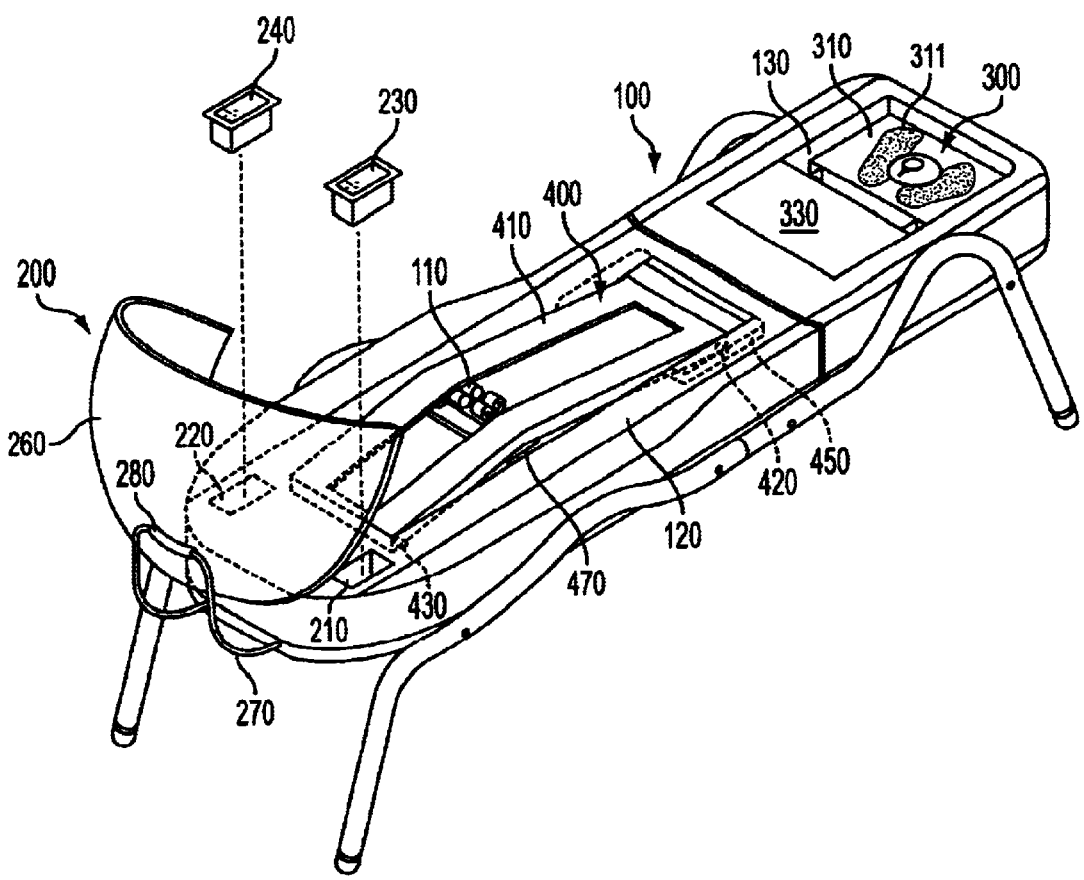
FIG. 3 is a perspective view illustrating the state that a capsule is opened in the hyperthermo-therapeutical apparatus according to the present invention.
Figure 4:
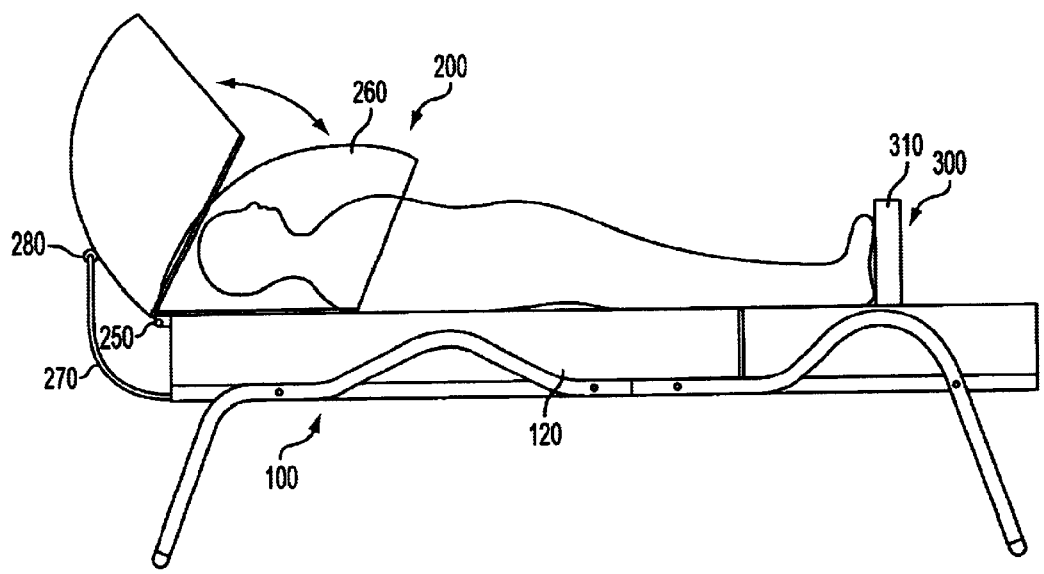
FIG. 4 is a side view of the state that the hyperthermo-therapeutical apparatus according to the present invention is used.
Figure 5:
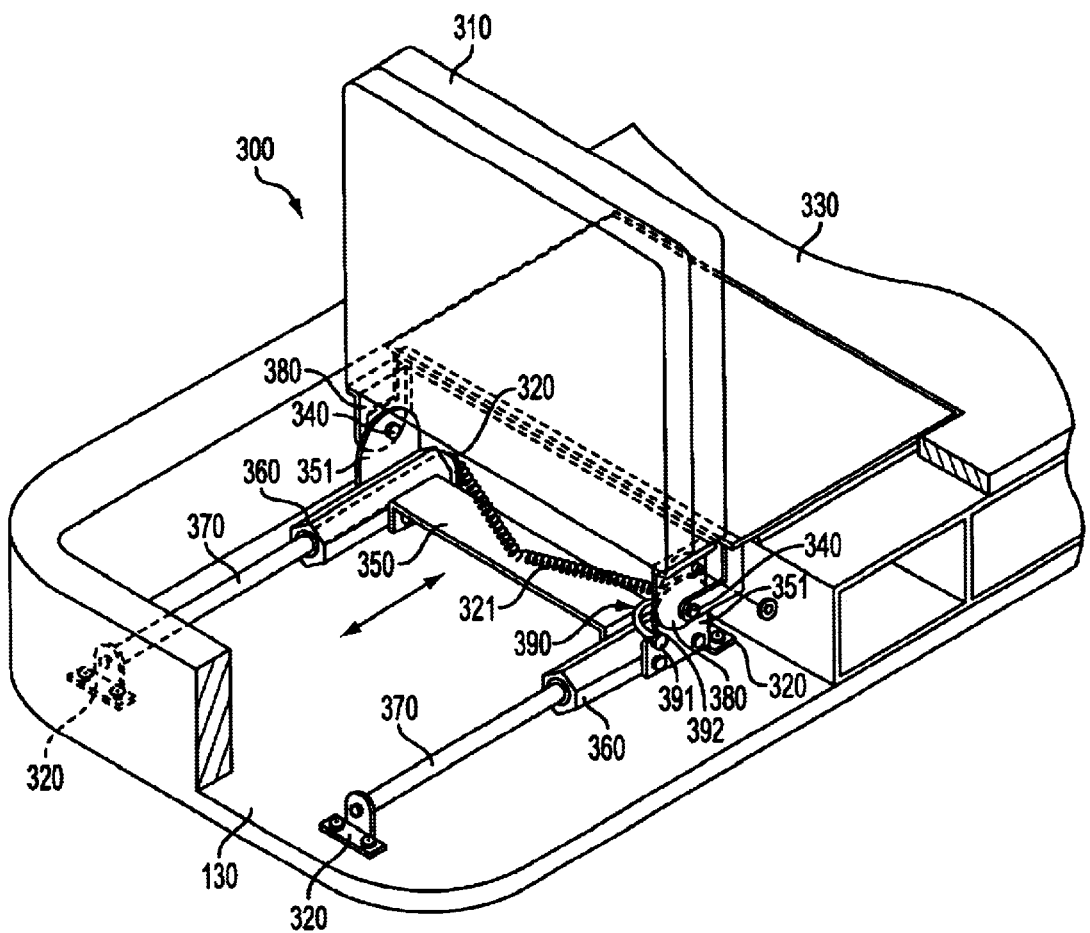
FIG. 5 is an extraction perspective view of a main portion of a foot pressure means according to the present invention.

More specifically, as illustrated in FIGS. 3 and 4, the sleep aid means 200 includes a humidifier mounting portion 210 and anion generator mounting portion 220 respectively formed at the portion corresponding to the head of the user at a predetermined interval from each other; a humidifier 230 and anion generator 240 respectively installed into the humidifier mounting portion 210 and anion generator mounting portion 220 and generating moisture and anions to the head of the user; and a capsule 260 for concentrating the moisture and anions generated from the humidifier mounting portion 210 and anion generator mounting portion 220 onto the head (facial) portion.

The capsule 260 closes parts of the head of the user so that the moisture and anions generated from the humidifier 230 and anion generator 240 are not leaked to the outside, one side of the lower end of the capsule 260 being connected to the body 120 by a hinge 250 to thus be opened and closed vertically.

One end of the capsule 260 is connected and fixed to the body 120 and the other end thereof is prevented from being pulled back further by a supporting rod 270 upwardly curved. A rubber packing 280 is connected to the upper end of the supporting rod 270 to prevent a scratch or damage on the capsule caused by a contact with the supporting rod 270.

Here, since the humidifier 230 and the anion generator 240 are commonly used technical items, a detailed description thereof will be omitted. They have a size being installable into the humidifier mounting portion 210 and anion generator mounting portion 220. In addition, the sleep aid means 200 is not limited to the humidifier 230 and the anion generator 240 employed as sleep requirements, but also an oxygen generator, an air cleaner and the like can be selectively used according to the circumstances if a sleep state can be optimized effectively.

As illustrated in FIGS. 5, 6a, 6b and 6c, the foot pressure means 300 includes a device space 130 of a predetermined size formed at the portion where the lower part of the body of the user is positioned, the upper part of which being opened; a slide shaft 370 positioned longitudinally on the device space 130, both end portions of which being fixed by a fixed bracket 320; a pair of housings 360 connected laterally slidable (i.e, left and right side direction) on the slide shaft 370 and connected integral with each other by a connection plate 350 to be moved in the same way; left and right connection brackets 380 connected to the left and right side walls 351 of the connection plate 350 by a connection shaft 340 and capable of moving around a predetermined section; a foot pressure board 310 of which bottom being engaged to the top surface of the connection bracket 380, provided with a plurality of pressure bosses 311 formed at its upper surface for applying a compress to the sole by adhering it to the sole of a user, and provided with a far infrared radiation lamp 312 electrically connected to the body 120 at its inside for radiating a large amount of far radiation rays; a foot missing prevention board 330 for preventing the missing of the foot of the user by moving onto the device space 130 as far as the foot pressure board moves forward when the foot pressure board 310 is forced to move forward according to the height of the user in the state that one end of the foot pressure board 310 is connected to the connection shaft 340 and is mounted to a guide groove 140 of the body 120; and a spring 321 of which one end being connected to the center of the connection plate 350 and of which the other end being connected to its respective fixed bracket 320 and which applies a spring force so that the foot pressure board 310 can be adhered to the sole of the user all the time.

The foot pressure board 310 maintains a vertical state on the device space 130 by a vertical maintenance means 390 when it is used, and it maintains a horizontal state when it is not used.

The upper end of the vertical maintenance means 390 is rotatably installed into one of the left and right connection brackets 380 and at the same time is fixed on the connection bracket 380 so that it is not pulled out by an engaging member. The lower end thereof is constructed such that an internally curved latch end 391 is installed and latched to a latch groove 392 formed at the side wall 351 of the connection plate 350 when the foot pressure board 310 positioned horizontally is lifted vertically.

Figure 7:
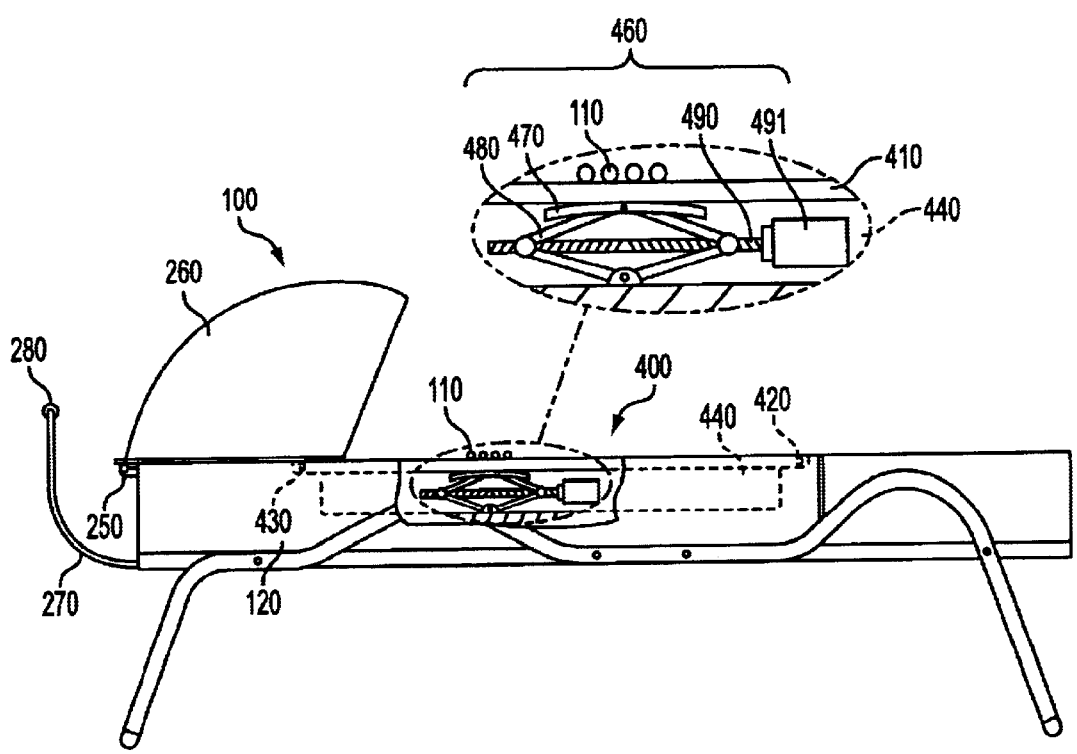
FIG. 7 is a side view illustrating the state of a vertebral correction means according to the present invention before it is operated.
Figure 8:
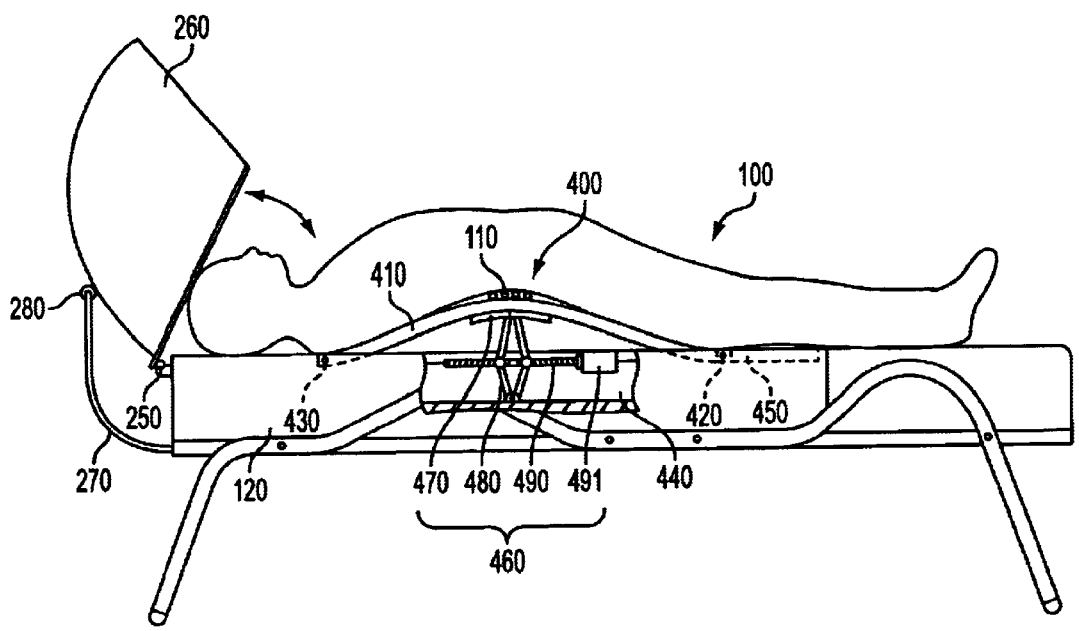
FIG. 8 is a side view illustrating the operation state of the vertebral correction means according to the present invention.

As illustrated in FIGS. 7 and 8, the vertebral correction means 400 includes a moving mat 410 which makes a user to be kept bent backward smoothly when the user lies on; a lift 460 which makes the moving mat bent in a bow shape; and a moving space 440 which satisfies the circumferential conditions so that the moving mat 410 can be bent in a bow shape by the lift 460.

The moving space 440 is formed at the upper end of the body 120 to have a predetermined length. It has a proper depth so that it is maintained vertical without being projected to the outside when the moving mat 410 is not lifted in the state that it is mounted at the moving space 440, and it is provided with a guide rail 450 at one end.

One side of the moving mat 410 is connected to the moving space 440 by a hinge 430, and the other side is provided with a roller 420 being laterally (left and right side direction) guided along the guide rail 450. As the roller 420 moves internally along the guide rail 450, the moving mat 410 serves to make the waist of the user bent backward smoothly as it is bent in a bow shape and is lifted to a proper height.

Such a moving mat 410 is entirely made of an elastic material so that it can be bent when it is lifted, or only a central portion directly bent, that is, a portion where the lift 460 is disposed, is made of the elastic material.

Here, means for bending the moving mat 410 in a bow shape are not limited to those in which the moving mat is made entirely of an elastic material or partially of the elastic material, a variety of means for forming only a directly bent portion in the form of joints or forming a cut groove at the lower side and bending the moving mat by this cut groove can be employed according to the circumstance if the moving mat can be bent in a bow shape when it is lifted.

The lift 460 is installed at the lower end of the center of the moving mat 410 and ascends or descends the moving mat according to the selection of the user. The lift 460 includes a fixing plate 470 tightly fixed to the bottom of the moving mat; a foldable link 480 longitudinally foldable of which the upper end being hingeably connected to the fixing plate 470 and of which the lower end being hingeably connected to the bottom of the moving space 440; a rotary screw 490 connected to the center of the foldable link 480 by a screw and longitudinally folding the foldable link 480; and a driving motor 491 for rotating the rotary screw 490.

Meanwhile, the construction and operation of the treatment unit 110 applying a hot compress to the vertebral acupuncture point of the user while moving around a predetermined section on the body 100 of the hyperthermo-therapeutical apparatus are not the technical information to be described in the present invention, but a commonly used technical information. So, a detailed description thereof will be omitted.

The operation of the sleep aid means 200, foot pressure means 300 and vertebral correction means 400 of the thusly constructed hyperthermo-therapeutical apparatus will now be described in turn.

Firstly, to use the sleep aid means 200, as shown in FIG. 3, the humidifier 230 and the anion generator 240 are installed respectively into the humidifier mounting portion 210 and the anion generator mounting portion 220, and these are electrically connected to the body 120. In this state, when the user lies on and the capsule 260 is closed, the capsule 260 closes the head portion of the user while moving around the hinge 250.

In this state, when a power is applied, moisture and anions are generated by the humidifier 230 and the anion generator 240. The generated moisture and anions are concentrated to the head portion of the user without being directly emitted to the outside since the capsule 260 closes the head portion of the user, so the user can take sleep in the optimum sleep state.

In addition, if the capsule 260 is lifted when the sleep aid means 200 is not used, the capsule 260 is prevented from being bent backward further by the support rod 270 and is prevented from being scratched or damaged by means of the rubber packing 280 when it is contacted with the support rod 270.

Figure 6A:
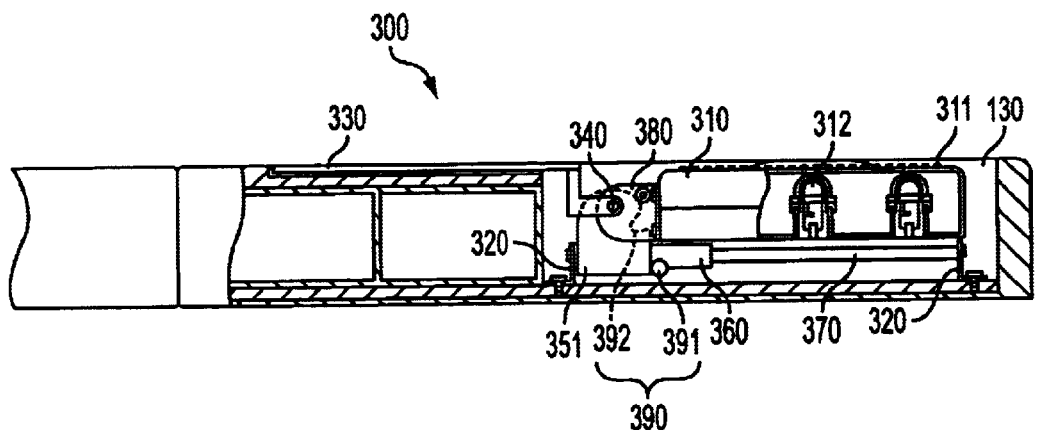
FIG. 6a is an enlarged cross sectional view of the main portion illustrating the state that the foot pressure means according to the present invention is contained in a device space.

With respect to the initial connection state of the foot pressure means 300, as shown in FIG. 6a, the foot pressure board 310 is installed horizontally in the device space 130, the latch end 391 of the vertical maintenance means 390 is kept pulled out from the latch groove 392 of the connection plate 350, and the foot missing prevention board 330 is mounted to the guide groove 140. At this time, the foot pressure means 300 is not used.

Figure 6B:
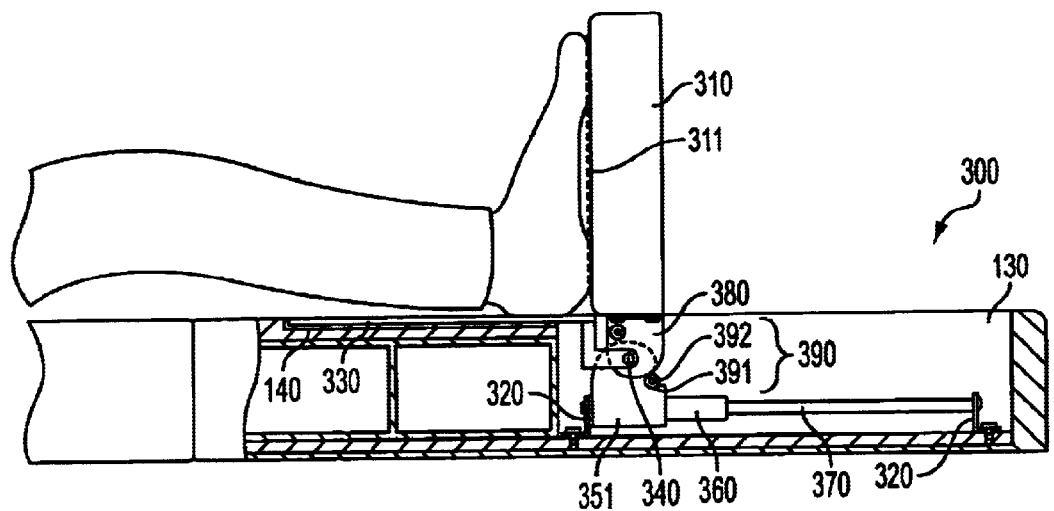
FIG. 6b is an enlarged cross sectional view of the main portion illustrating the state that the foot pressure means according to the present invention is used.
Figure 6C:
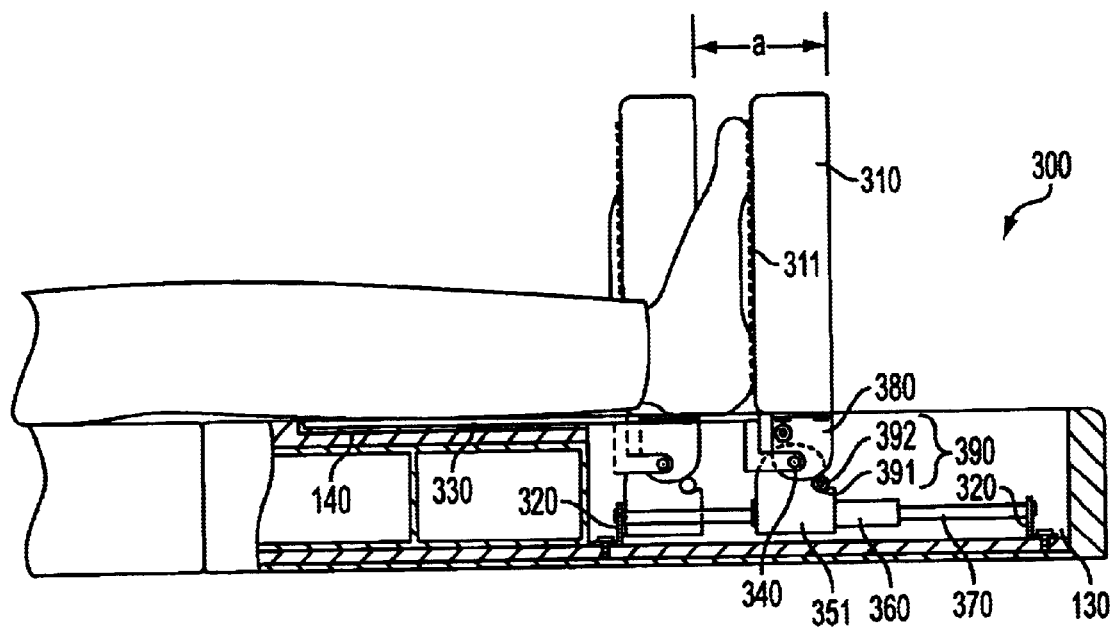
FIG. 6c is an enlarged cross sectional view of the main portion illustrating the state that the foot pressure means according to the present invention is moved forward by a user.

In this state, to use the foot pressure means 300, firstly, when the foot pressure board 310 is lifted upwardly, it becomes a vertical state while moving around the connection shaft 340 along with the connection bracket 380. At this time, as illustrated in FIG. 6b, the upper end of the vertical maintenance means 390 is rotatably connected onto the connection bracket 380, the latch end 391 is installed and latched to the latch groove 392 smoothly during the step of rotatably moving to the upper part along with the foot pressure board 310, thus maintaining the foot pressure board a vertical state.

In this state, when the user lies on the body, the sole of the user is contacted with the pressure boss 311 of the foot pressure board 310. At this time, when the foot missing prevention board 330 is stretched out in the state the user makes its foot small, the foot pressure board 310 overcomes the tensile force of the spring 321 and then moves forward. This is because the housing 360 moves forward along the slide shaft 370 and the moving housing 360 is connected integrally with the foot pressure board 310, the foot missing prevention board 330 and the like by the medium of the connection shaft 340.

Meanwhile, the foot pressure board 310 is forcibly adhered to the sole of the user by the tensile force of the spring 321. Thus, since the pressure boss 311 applies a compress to the sole of the user a bit forcibly and the far infrared radiation lamp 312 installed internally emits a large amount of far infrared radiation rays to the sole, both compress and heating can be performed. Since the foot missing prevention board 330 moves along with the foot pressure board 310, it moves as far as the foot pressure board 310 moves and blocks an empty space (a) of the device space 130, for thereby preventing the missing of the foot of the user into the device space 130.

On the contrary, in case of not using the foot pressure means 300, the latch end 391 of the vertical maintenance means 390 is pulled out from the latch groove 392 and then is stored on the device space 130 in the state that the foot pressure board 310 is made horizontal.

To use the vertebral correction means, as illustrated in FIG. 7, in the state that the lift 460 is hingeably connected between the moving mat 410 and the body 120, the foldable link 480 is stretched out and the moving mat 410 is mounted and fixed on the moving space 440.

In this state, a hot compress is applied to the vertebra by using the treatment unit 110 of the hyperthermo-therapeutical apparatus as in the conventional method. When it is desired to correct the waist, the treatment unit is disposed to the waist portion of the user and then a power is applied to the driving motor 491.

At this time, when the rotary screw 491 is rotated by the driving motor 491, the foldable link 480 is folded internally as in the vehicle jockey method and is ascended. By this ascending operation, the moving mat 410 is bent in a bow shape.

One side of such a moving mat 410 is connected by a hinge 430 and the other side thereof is provided with a roller 420 so that it can be moved, and the moving mat 410 itself is made of an elastic material or the center portion directly bent is made of the elastic material. Therefore, when the lift 460 is ascended, the roller 420 is bent in a bow shape while moving internally along the guide rail 450.

Then, the waist of the user is bent backward smoothly as shown in FIG. 8. On the contrary, if the driving motor 491 is reversely rotated, it is restored to the original state. When such a method is repeated, the waist is tightened and relaxed and the elasticity and muscle force of the vertebral acupuncture point is improved, thereby correcting the vertebra.

At this time, the treatment unit 110 is disposed at the waist of the user and applies a hot compress, thus correcting the vertebra more effectively.

The thusly operated hyperthermo-therapeutical apparatus 100 is available for an exclusive use for a hyperthermo-therapeutical apparatus, and also it can perform treatment by including the sleep aid means 200, foot pressure means 300 and vertebral correction means 400 according to the selection of the user.

As seen from above, according to the present invention, since the hyperthermo-therapeutical apparatus for applying a hot compress to the vertebral acupuncture point of the user is provided with the sleep aid means, anions and moisture can be supplied into the capsule through the sleep aid means when the sleep aid means is used. Thus, an optimum sleep condition is maintained, thus performing a hyperthermo-therapy while having a good sleep.

Moreover, since the hyperthermo-therapeutical apparatus for applying a hot compress to the vertebral acupuncture point of the user is provided with the foot pressure means, the sole is pressurized when the foot pressure means is used, thereby helping blood circulation and preventing a variety of geriatric diseases.

Furthermore, since the hyperthermo-therapeutical apparatus for applying a hot compress to the vertebral acupuncture point of the user is provided with the vertebral correction means, a hot compress can be applied to the vertebra as in the conventional art and of course the operation of bending the waist of the user backward is repeated to thus tighten and relax the waist, thereby improving the elasticity and muscle force of the vertebral acupuncture point and correcting the vertebra.

While the invention has been shown and described with reference to certain preferred embodiments thereof, it will be understood by those skilled in the art that various changes in form and details may be made therein without departing from the spirit and scope of the invention as defined by the appended claims.

What is claimed is:

1. A multifunction hyperthermo-therapeutical apparatus in which a treatment unit is installed on a body of a mat type and this treatment unit applies a hot compress to the vertebral acupuncture point of a patient while it is moved around a predetermined section by a driving transmission device, wherein the multifunction hyperthermo-therapeutical apparatus comprising:

a sleep aid means installed at the portion corresponding to the front surface of the body for generating anions and moisture mostly on the head portion of a user;

a foot pressure means installed to the portion corresponding to the rear surface of the body for applying a hot compress on the sole of the user; and a vertebral correction means installed at the center of the body between the sleep aid means and the foot pressure means for raising the waist of the user to a predetermined height and tightening and relaxing the vertebral acupuncture point.

2. The multifunction hyperthermo-therapeutical apparatus of claim 1, wherein the sleep aid means includes a humidifier mounting portion and anion generator mounting portion respectively formed at the portion corresponding to the head of the user at a predetermined interval from each other; a humidifier and anion generator respectively installed into the humidifier mounting portion and anion generator mounting portion and generating moisture and anions to the head of the user; a capsule for closing parts of the head of the user so that the moisture and anions generated from the humidifier and anion generator are not leaked to the outside, one side of the lower end of the capsule being connected to the body by a hinge to thus be opened and closed vertically; a support rod in which its one end is connected and fixed to the body and the other end thereof is prevented from being pulled back further upwardly curved; and a rubber packing connected to the upper end of the supporting rod to prevent a scratch or damage on the capsule caused by a contact with the supporting rod.

3. The multifunction hyperthermo-therapeutical apparatus of claim 1, wherein the foot pressure means includes a device space of a predetermined size formed at the portion where the lower part of the body of the user is positioned, the upper part of which being opened; a slide shaft positioned longitudinally on the device space, both end portions of which being fixed by a fixed bracket; a pair of housings connected laterally slidable (i.e, left and right side direction) on the slide shaft and connected integral with each other by a connection plate to be moved in the same way; left and right connection brackets connected to the left and right side walls of the connection plate by a connection shaft and capable of moving around a predetermined section; a foot pressure board of which bottom being engaged to the top surface of the connection bracket, provided with a plurality of pressure bosses formed at its upper surface for applying a compress to the sole by adhering it to the sole of a user, and provided with a far infrared radiation lamp electrically connected to the body at its inside for radiating a large amount of far radiation rays; a foot missing prevention board for preventing the missing of the foot of the user by moving onto the device space as far as the foot pressure board moves forward when the foot pressure board is forced to move forward according to the height of the user in the state that one end of the foot pressure board is connected to the connection shaft and is mounted to a guide groove of the body; and a spring of which one end being connected to the center of the connection plate and of which the other end being connected to its respective fixed bracket and which applies a spring force so that the foot pressure board can be adhered to the sole of the user all the time.

4. The multifunction hyperthermo-therapeutical apparatus of claim 3, wherein the foot pressure board maintains a vertical state on the device space by a vertical maintenance means when it is used, and it maintains a horizontal state when it is not used.

5. The multifunction hyperthermo-therapeutical apparatus of claim 4, wherein the upper end of the vertical maintenance means is rotatably installed into one of the left and right connection brackets and at the same time is fixed on the connection bracket so that it is not pulled out by an engaging member and the lower end thereof is constructed such that an internally curved latch end is installed and latched to a latch groove formed at the side wall of the connection plate when the foot pressure board positioned horizontally is lifted vertically.

6. The multifunction hyperthermo-therapeutical apparatus of claim 1, wherein the vertebral correction means includes a moving space formed at the upper end of the body to have a predetermined length and provided with a guide rail at one end thereof, a moving mat in which its one end is connected to the moving space by a hinge, and the other side is provided with a roller being laterally (left and right side direction) guided along the guide rail and when the roller moves internally along the guide rail, the moving mat serves to make the waist of the user bent backward smoothly as it is bent in a bow shape and is lifted to a proper height; and a lift installed at the lower end of the center of the moving mat for ascending and descending the moving mat according to the selection of the user.

7. The multifunction hyperthermo-therapeutical apparatus of claim 6, wherein the lift includes a fixing plate tightly fixed to the bottom of the moving mat; a foldable link longitudinally foldable of which the upper end being hingeably connected to the fixing plate and of which the lower end being hingeably connected to the bottom of the moving space; a rotary screw connected to the center of the foldable link by a screw and longitudinally folding the foldable link; and a driving motor for rotating the rotary screw.

8. The multifunction hyperthermo-therapeutical apparatus of claim 6, wherein such a moving mat is entirely made of an elastic material so that it can be bent when it is lifted, or only a central portion directly bent, that is, a portion where the lift is disposed, is made of the elastic material.

* * * * *